(12) United States Patent
Wittenberger et al.

(10) Patent No.: US 6,579,287 B2
(45) Date of Patent: Jun. 17, 2003

(54) CRYOSURGICAL ABLATION DEVICE HAVING SEQUENTIAL INJECTION AND METHOD THEREFOR

(75) Inventors: Dan Wittenberger, Pierrefonds (CA); Benoit Thibault, Coteau-du-Lac (CA); Sean M. Carroll, Beaconsfield (CA); Tara Zerby, Germantown, WI (US)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/973,595

(22) Filed: Oct. 9, 2001

(65) Prior Publication Data

US 2003/0069568 A1 Apr. 10, 2003

(51) Int. Cl.⁷ .............................................. A61B 18/18
(52) U.S. Cl. ........................................... 606/21; 606/23
(58) Field of Search ...................... 606/20–26

(56) References Cited

U.S. PATENT DOCUMENTS

| | | |
|---|---|---|
| 5,147,355 A | 9/1992 | Friedman et al. |
| 5,281,213 A | 1/1994 | Milder et al. |
| 5,281,215 A | 1/1994 | Milder |
| 5,423,807 A | 6/1995 | Milder |
| 5,759,182 A | 6/1998 | Varney et al. |
| 5,807,391 A | 9/1998 | Wijkamp |
| 6,106,518 A | 8/2000 | Wittenberger et al. |
| 6,235,019 B1 | 5/2001 | Lehmann et al. |
| 6,270,493 B1 | 8/2001 | Lalonde et al. |
| 6,280,439 B1 | 8/2001 | Martin et al. |
| 6,355,029 B1 * | 3/2002 | Joye et al. .................... 606/21 |

* cited by examiner

Primary Examiner—Linda C. M. Dvorak
Assistant Examiner—David M. Ruddy
(74) Attorney, Agent, or Firm—Christopher & Weisberg, P.A.

(57) ABSTRACT

A device and method for cryosurgical ablation. A tip has a thermally transmissive region along a length thereof in which the thermally transmissive region is operable at a temperature sufficient to cryosurgically ablate tissue in contact therewith. A plurality of cryosurgical fluid injection lumens each have a first end positioned within the tip at a different point along the length of the thermally transmissive region. Each of the first ends is arranged to cool overlapping respective portions along the length of the thermally transmissive region when cryogenic fluid is ejected from the plurality of cryogenic fluid injection lumens.

20 Claims, 3 Drawing Sheets

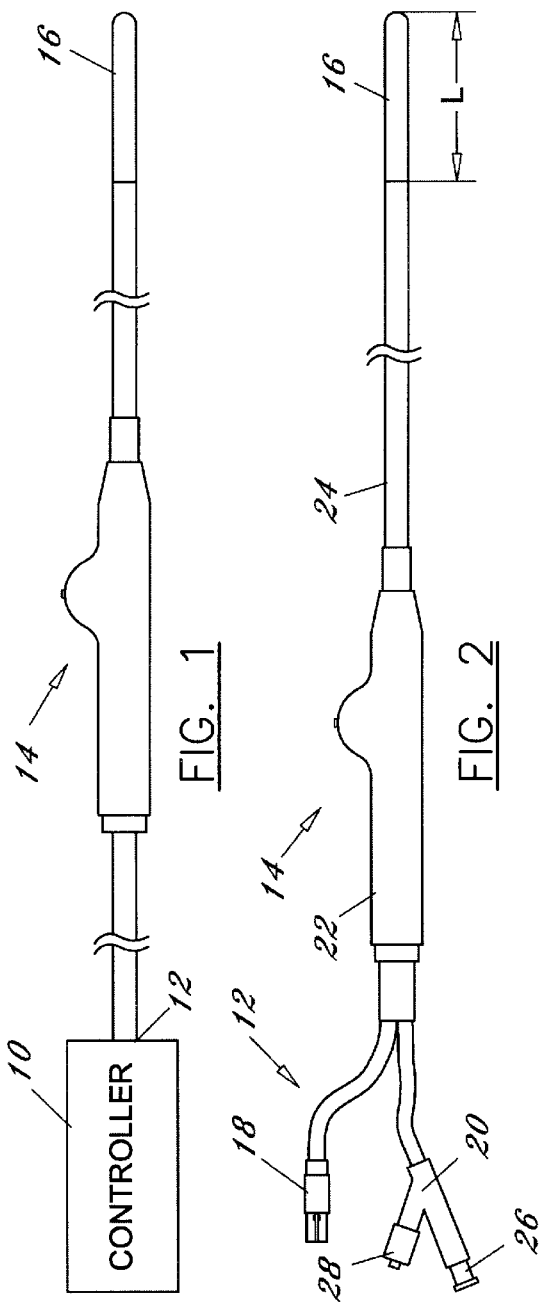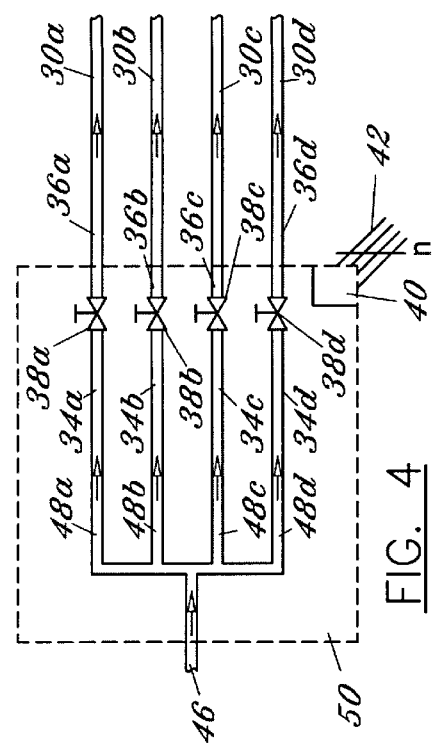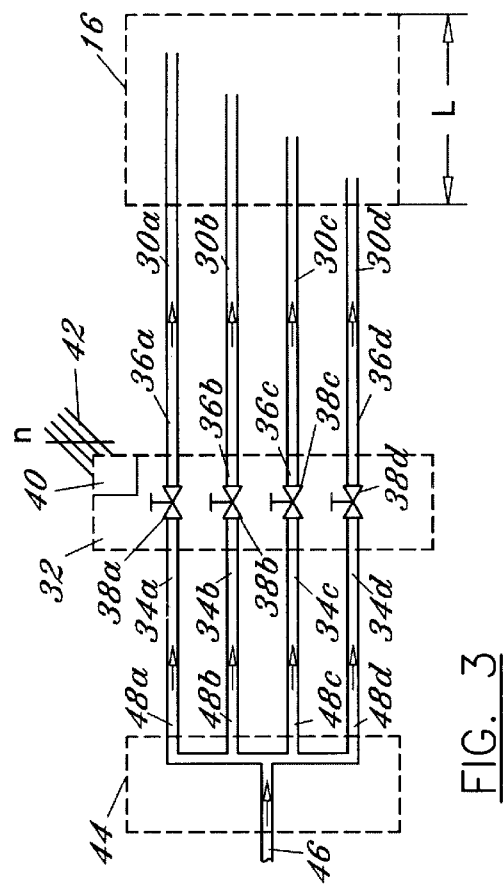

CRYOSURGICAL ABLATION DEVICE HAVING SEQUENTIAL INJECTION AND METHOD THEREFOR

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to cryosurgical tissue ablation, and in particular, to a device and method which increases the effective freezing length in the device tip while simultaneously maintaining a usable device size and safe operating characteristics.

BACKGROUND OF THE INVENTION

Advances in medical procedures have resulted in the development of procedures which use minimally invasive surgical techniques such that one or more slender implements such as probes or catheters are inserted through one or more small incisions into a patent's body. These implements include surgical ablation implements having a rigid or flexible structure in which the ablation device is located at or near the implement's distal end that is placed adjacent to the tissue to be ablated.

Radio frequency energy, microwave energy, laser energy, extreme heat and extreme cold can be provided by the ablation device to kill the tissue. Certain procedures, such as cardiac procedures, are performed by selectively ablating the tissue. For example, in the case of a cardiac arrhythmia, the cardiac tissue is selectively ablated to eliminate the source of the arrhythmia. A popular minimally invasive procedure using radio frequency (RF) catheter ablation, has been used as has cryoablation in which the RF and cryogenic devices are arranged to provide very limited spot-sized lesions. As such, these conventional devices are not well suited for tissue ablation along a length, i.e. larger than a spot-sized lesion.

In order to achieve freezing ablation along a length using conventional devices, a series of spot ablation lesions are created by moving the device tip located at the distal end of the device along the length to be ablated. The device typically includes a single cryogenic fluid lumen. Use of this arrangement can be time consuming, thereby prolonging procedure duration, and can result in an uneven ablation, reducing the effectiveness of the procedure. It would therefore be desirable to have a cryosurgical device that provides enhanced cooling capability for spot lesions, as well as the capability to create other than spot lesions.

SUMMARY OF THE INVENTION

The present invention provides a device that provides enhanced cooling capability for spot lesions and the capability to create other than spot lesions, as well as a method for ablating tissue. In an exemplary embodiment the device includes a tip having a thermally transmissive region along a length thereof. The thermally transmissive region is operable at a temperature sufficient to cryosurgically ablate tissue in contact therewith. Fluid injection lumens are positioned within device so that the ends of the lumens are at different points along the length of the thermally transmissive region. Each of the ends are arranged to cool overlapping portions along the length of the thermally transmissive region when cryogenic fluid is ejected from the the fluid injection lumens.

In an exemplary method for cryosurgically ablating tissue, a cryosurgical tip is positioned at tissue to be ablated, the tip having a thermally transmissive region along a length thereof. Cryogenic fluid is sequentially injected into the tip through multiple cryogenic fluid injection lumens terminating within the tip at different points along the length of the thermally transmissive region.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is a schematic illustration of a cryosurgical system utilizing a cryogenic cooling structure constructed in accordance with the principles of the present invention;

FIG. 2 is a diagram of a side view of an exemplar catheter arranged in accordance with the principles of the present invention;

FIG. 3 is a block diagram of an arrangement of longitudinally spaced injection lumens and their corresponding cryogenic fluid control valves;

FIG. 4 is a block diagram of an integrated fluid provisioning unit;

DETAILED DESCRIPTION OF THE INVENTION

Figure 5:
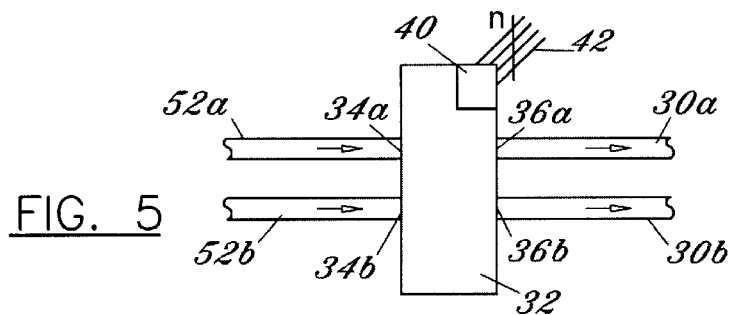
FIG. 5 is a block diagram of a two port cryogenic fluid valve assembly.

Referring now to the drawing figures in which like reference designators refer to like elements, there is shown in FIG. 1 a schematic illustration of a cryosurgical system utilizing a cryogenic cooling structure constructed in accordance with the principles of the present invention. The system includes a fluid controller 10 coupled to the proximal end 12 of a catheter 14. The controller 10 allows or causes cryogenic fluid to flow from a cryogenic fluid supply (not shown) through the proximal end 12 of the catheter 14 to a thermally transmissive tip region 16 positioned at the distal end of the catheter 14. In operation, the fluid controller 10 is responsive to an input from a foot pedal or other human actuable switch to permit the flow of cryogenic fluid into the catheter 14. One or more temperature sensors (not shown) in electrical communication with the controller 10 can be provided to regulate or terminate the flow of cryogenic fluid into the catheter 14 by a predetermined temperature at a selected point or points on or within the catheter such as in thermally transmissive region 16 is obtained.

The cryogenic fluid can be in a liquid or a gas state. An extremely low temperature can be achieved within the thermally transmissive region 16 by cooling the fluid to a predetermined temperature prior to its introduction into the catheter 14, by allowing a liquid state cryogenic fluid to boil or vaporize, or by allowing a gas state cryogenic fluid to expand.

Exemplary liquids include chlorodifluoromethane, polydimethylsiloxane, ethyl alcohol, HFCs such as AZ-20 (a 50-50 mixure of difluoromethane and pentafluoroethane sold by Allied Signal), nitrous oxide, and CFCs such as DuPont's Freon. Exemplary gases include nitrous oxide and carbon dioxide.

FIG. 2 is a diagram of a side view of an exemplar catheter 14 arranged in accordance with the principles of the present invention. As shown in FIG. 2, the catheter 14 preferably includes an electrical connector 18 and a mechnaical connector 20 coupled to the thermally transmissive region 16 via a flexible segment 24.

The electrical connector 18 is coupled to the controller 10 and provides external connection points for electronic signals such as cryogenic fluid valve activation signals, ECG signals, temperature sensing signals and the like. The cryogenic connector 20 preferably has an input opening 26 by which cryogenic fluid is input into the catheter 14 and a cryogenic output opening 28 by which the cryogenic fluid is evacuated from the catheter 14.

The handle 22 is gripped by the user during operation and includes those control elements necessary for the user to "steer" the catheter inside the patient's body. Further, the handle 22 an be arranged to define an inner volume in which cryogenic fluid valves are located. The arrangement and operation of the cryogenic fluid valves are discussed below in detail.

Flexible segment 24 is generally arranged to include an outer fluid and gas impermeable sheath inside of which one or more flexible cryogenic fluid (or vapor) lumen are disposed for carrying the cryogenic fluid from the controller 10 to the thermally transmissive region 16 and returning it. Preferably, the outer flexible sheath includes a return lumen or defines a volume for use as the return path for cryogenic fluid from the thermally transmissive region 16 to the cryogenic output opening 28. Arrangements for providing a cryogenic fluid return lumen or using all or a portion of an inner volume of the flexible segment 24 as a return path for cryogenic fluid are known.

In operation, the cryogenic fluid is provided via the controller 10 to the cryogenic fluid input opening 26. By applying a negative pressure to the cryogenic output opening 28, the cryogenic fluid is circulated through the handle 22, through the flexible segment 24 to the thermally transmissive tip region 16 where the fluid expands, boils, etc., thereby cooling the thermally transmissive region 16. The spent vapor is returned through the flexible segment 24, through the handle 22 and out the cryogenic fluid output opening 28.

The catheter 14 is preferably arranged to include a plurality of cryogenic fluid injection lumens having respective openings longitudinally spaced at different points along the length L of the thermally transmissive region 16. As discussed below in detail, the plurality of injection lumens can be individually arranged to span the entire length of the catheter 14 from the input opening 26 to the thermally transmissive region 16 or can be arranged as a single injection lumen from the input opening 26 to a cryogenic fluid distribution element provided in the handle 22.

FIG. 3 shows a block diagram of an arrangement of the plurality of longitudinally spaced injection lumens and their corresponding cryogenic fluid control valves. Initially, it is noted that although FIG. 3 and the subsequent figures are arranged to show two or four injection lumens, it is contemplated that any quantity of injection lumen can be used subject to the desired length of the thermally transmissive region 16, the maximum acceptable diameter of the flexible segment 24 for a particular application and the cryogenic fluid input capacity of the system.

As shown in FIG. 3, the injection lumens 30a, 30b, 30c and 30d couple the cryogenic fluid valve assembly 32 to the thermally transmissive region 16 at the tip of catheter 14. Each of the injection lumens 30a–30d terminate at a different point along length L within the thermally transmissive region 16 or the shaft 24. For example, as shown in FIG. 3, the injection lumen 30a is the longest injection lumen, terminating substantially at the distal end of the catheter 14. The injection lumen 30b is shorter than the injection lumen 30a, the injection lumen 30c is shorter than the injection lumen 30b and the injection lumen 30d is shorter than the injection lumen 30c such that it is positioned at a point along the length L within the thermally transmissive region 16 closer to the handle 22 than the injection lumens 30a–c.

The cryogenic fluid valve assembly 32 is preferably comprised of an assembly fluid input 34 for each of the injection lumen (shown as assembly fluid inputs 34a, 34b, 34c and 34d in FIG. 3) in fluid communication with a corresponding assembly fluid output 36 (shown as assembly fluid outputs 36a, 36b, 36c and 36d in FIG. 3) via a corresponding valve 38 (shown as valves 38a, 38b, 38c and 38d in FIG. 3). Each of the assembly fluid outputs 36a–36d is coupled to and is in fluid communication with a corresponding injection lumen 30a–30d. Each of the valves 38a–38d are individually actuable by mechanical, electrical or electromechanical operation.

As shown in FIG. 3, the cryogenic fluid valve assembly 32 includes a valve processor 40 which receives n electronic actuation signals via the corresponding electronic actuation signal lines 42 and where n is the number of signal lines necessary to control actuation of the valves 38. The valve processor 40 can be any processing unit capable of actuating the valves 38. For example, the valves 38 can be arranged as piezo-electric valves which are actuable based on well-known piezo-electric principles. In this case, the valve processor 40 operates to control the piezo-electric effect necessary to actuate the valves 38. The piezo-electric actuation method for the cryogenic fluid valve assembly 32 is preferred because the assembly 32 can be manufactured in a size small enough for placement within the handle 22 of the catheter 14. Of course, those skilled in the art understand that any suitable method for actuating the valves 38 can be used.

Also as shown in FIG. 3, the cryogenic fluid path includes a cryogenic fluid distributor 44 having an input 46 and one or more outputs 48 (shown in FIG. 3 as outputs 48a, 48b, 48c and 48d) corresponding to assembly fluid inputs 34. The cryogenic fluid distributor 44 is preferably made of any material which can withstand cryogenic fluid temperatures and which can be manufactured in a size small enough to be positioned within the handle 22 of the catheter 14. In the case where the cryogenic fluid distributor 44 is positioned within the handle 22, the input 46 is coupled to the cryogenic connector 20 by a tube suitable for carrying cryogenic fluid.

Although the cryogenic fluid valve assembly 32 and the cryogenic fluid distributor 44 are shown as separate elements in FIG. 3, it is contemplated that the cryogenic fluid valve assembly 32 and the cryogenic fluid distributor 44 can be provided as a single unit. FIG. 4 is a block diagram showing the integrated fluid provisioning unit 50 which includes the input 46, the valves 38 and the assembly fluid outputs 36. The integrated fluid provisioning unit 50 is preferably located within the inner volume of the handle 22 but can also be located in other system components such as the controller 10. For example, the valves can be in a distal portion of the catheter.

Inclusion of the fluid distribution component, whether in the form of cryogenic fluid distributor 44 as shown in FIG. 3 or within the integrated fluid provisioning unit 50 as shown in FIG. 4, advantageously allows a single fluid connection between the catheter 14 and the controller 10.

The present invention may also be arranged without the cryogenic fluid distributor 44 or the integrated fluid provisioning unit 50. FIG. 5 shows an example of a two port cryogenic fluid valve assembly 32 having two assembly fluid inputs 34a and 34b and two assembly fluid outputs 36a and 36b coupled to corresponding injection lumens 30a and 30b. Valves 38 are not shown in FIG. 5 for the sake of simplicity, it being understood that the valves 38 are included as described above with respect to the cryogenic fluid valve assembly 32. Using the arrangement shown in FIG. 5, corresponding input lumen 52 (shown in FIG. 5 as input lumens 52a and 52b) are required to couple the controller 10 to the catheter 14 (via the cryogenic connector 20). An arrangement similar to the cryogenic fluid valve assembly 32 shown in FIG. 5 is implemented in the case where the cryogenic fluid distributor 44 is positioned in the controller 10 and the cryogenic fluid valve assembly 32 is located in the handle 22.

Figure 6:
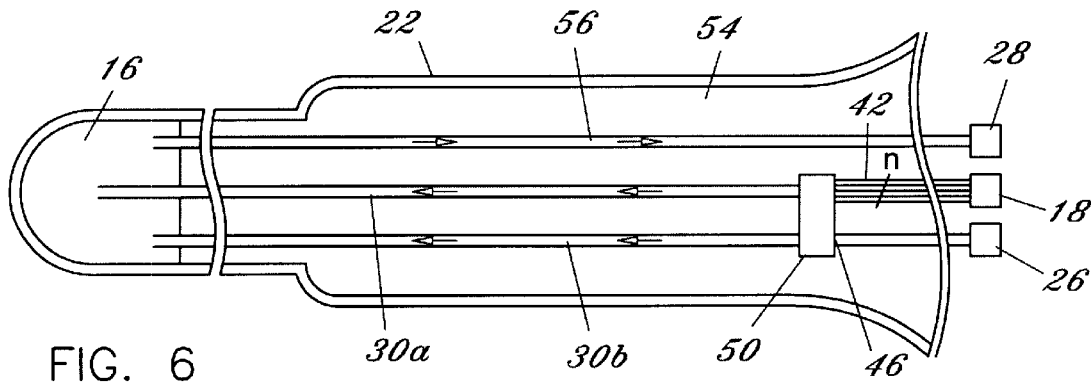
FIG. 6 is a cut away side view of an integrated fluid provisioning unit positioned within the inner volume of a handle.

FIG. 6 shows a cut away side view of an example of an integrated fluid provisioning unit 50 positioned within the inner volume 54 of a handle 22. As shown in FIG. 6, the injection lumens 30a and 30b couple the integrated fluid provisioning unit 50 to the thermally transmissive tip region 16. A return lumen 56 is provided for evacuating the cryogenic fluid from the thermally transmissive tip region 16 for return to the fluid reservoir 10. The return lumen 56 is coupled to the cryogenic output opening 28, the electronic actuation signal lines 42 are coupled to the electrical connector 18 and the cryogenic fluid input 46 is coupled to the input opening 26.

As discussed above with reference to FIGS. 3 and 4, it is contemplated that the cryogenic fluid distributor 44 and/or the cryogenic fluid valve assembly 32 can be located within the inner volume 54 of the handle 22.

Figure 7:
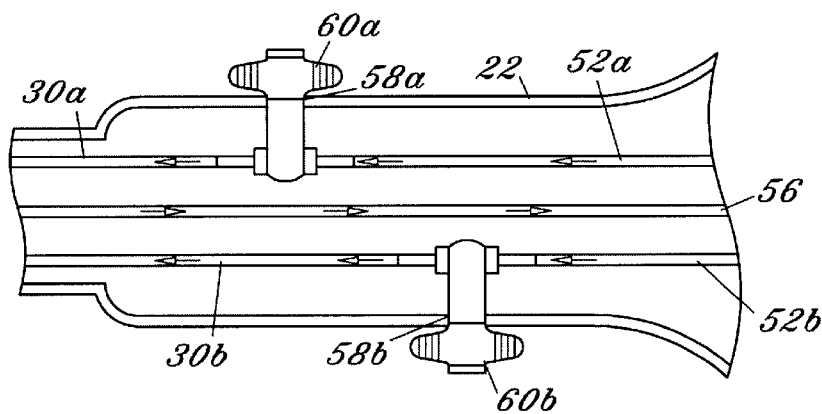
FIG. 7 is a cut away side view of an alternate arrangement of the present invention of thumbscrews positioned within the inner volume of a handle.

FIG. 7 shows a cut away side view of an alternate arrangement of the present invention in which the cryogenic fluid flow is manually actuated by thumbscrew valves 58a and 58b. As shown in FIG. 7, the human actuable portion of the thumbscrew valves 58a and 58b protrude through the outer surface of the handle 22a as thumbscrews 60a and 60b, respectively. The thumbscrew valves 58a and 58b are manually adjustable by the user via a corresponding thumbscrew 60a and 60b to open or close the cryogenic fluid path between the input lumens 52a and 52b and the corresponding injection lumen 30a and 30b. Although the arrangement using manually operated valves can be implemented, the preferable arrangement is using a processor controlled electronic or electro-mechanical switch. The reasoning behind this preference is discussed below in detail with respect to the sequential operation of the lumens 30 in the catheter 14.

Figure 8A:
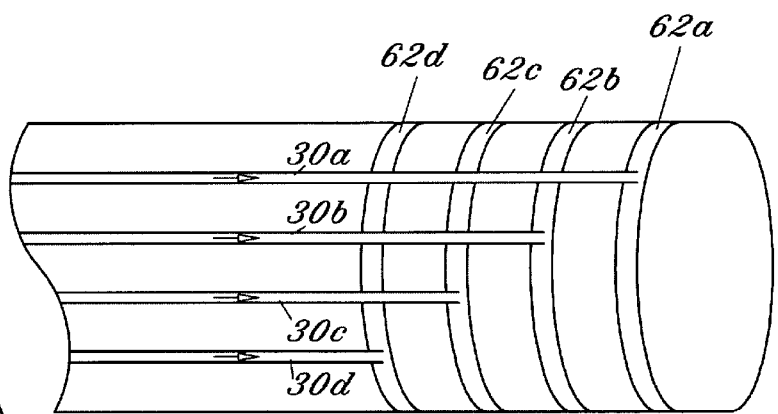
FIGS. 8A–E show diagrammatic views of the thermally transmissive tip region at various times during the sequential operation of the valves.

The operation of the catheter 14 is described with reference to FIGS. 8A–8E. Each of FIGS. 8A–8E show a diagrammatic view of the thermally transmissive tip region 16 at various times during the sequential operation of the valves 38a–38d. FIG. 8A shows the thermally transmissive tip region 16 at a state in which none of valves 38a–38d have been opened, i.e. cryogenic fluid is not flowing in the injection lumens 30a–30d. The freeze zones 62a, 62b, 62c and 62d show those areas on the surface of the thermally transmissive tip region 16 corresponding to the distal terminus of a corresponding injection lumen 30a–30d. It is noted that the freeze zones 62a–62d represent approximate areas along the surface of the thermally transmissive tip region 16 and do not correspond to actual elements. As such, the size and specific location of the freeze zones 62a–62d can vary and are substantially related to the corresponding distal terminus of the injection lumen 30a–30d.

Figure 8B:
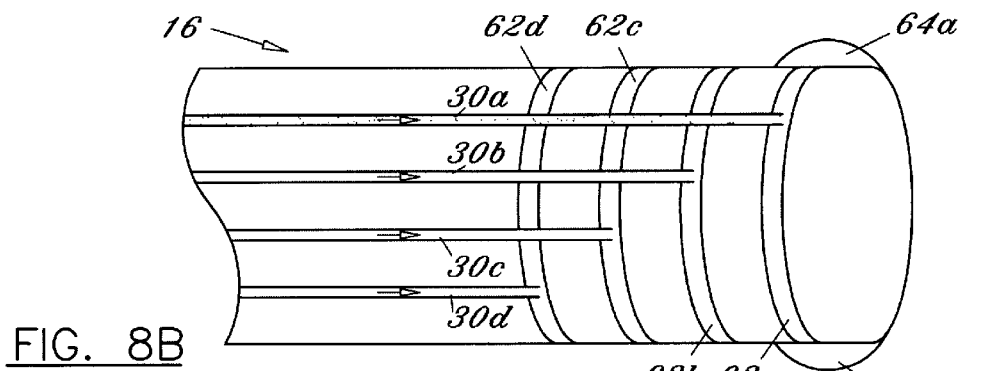
Figure 8C:
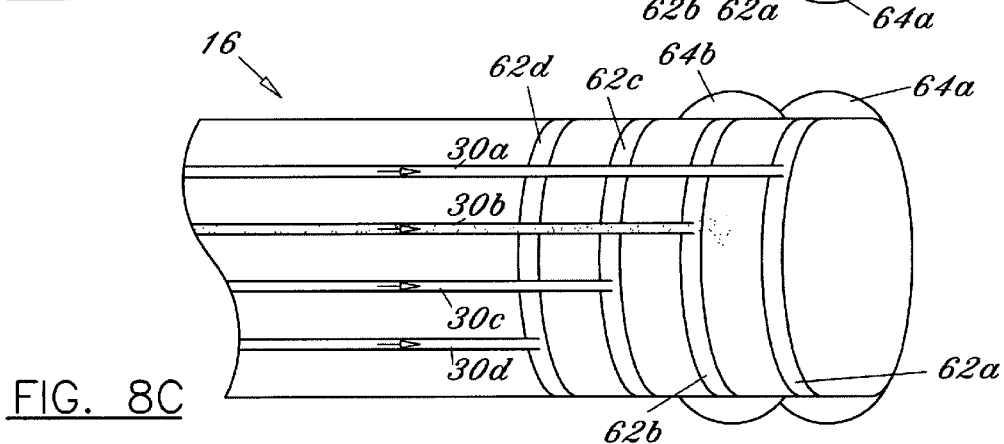

Upon actuation of the device, the valves 38a–38d are sequentially opened and closed. FIG. 8B shows cryogenic fluid in injection lumen 30a causing a freezing condition around the freeze zone 62a. As such, the area 64a on the exterior of the thermally transmissive tip region 16 is cooled by the ejection of the cryogenic fluid from the distal terminus of the injection lumen 30a such that the area 64a is cooled to an extent sufficient for the application of cryosurgical ablation. At a point t in time after the valve 38a is opened, the valve 38a is closed and the valve 38b is opened, causing cryogenic fluid to be ejected from the distal end of the injection lumen 30b in the thermally transmissive tip region 16. As a result, the area 64b around the freeze zone 62b is created which overlaps the area 64a and is chilled to a point sufficient for cryosurgical ablation.

Figure 8D:
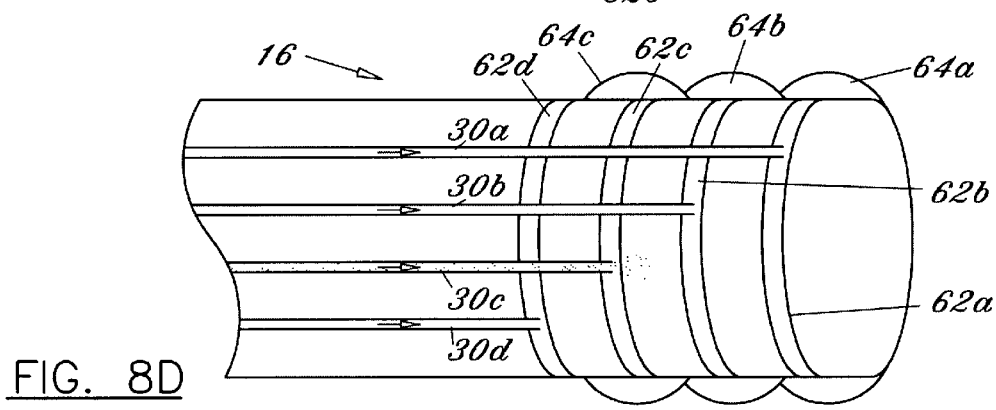
Figure 8E:
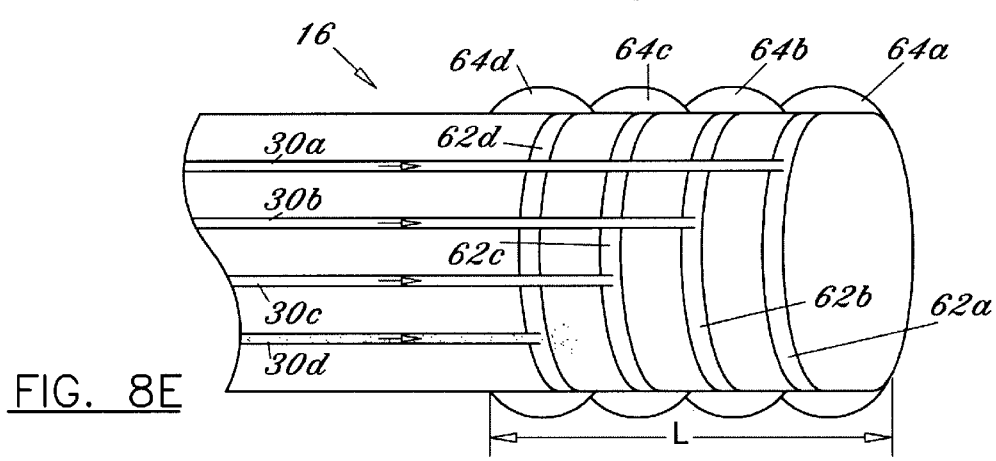

FIG. 8D and FIG. 8E are diagrams showing the expansion of the freeze area to include overlapping areas 64c and 64d as a result of the sequential actuation of the valves 38c and 38d, respectively. As shown in FIG. 8E, the resultant freeze area occupies a length L along the thermally transmissive tip region 16.

The freeze area along length L is advantageously accomplished by sequentially operating the valves 38a–38d in a manner which does not require an excessive cryogenic fluid flow rate which would otherwise create a positive pressure inside the catheter 14. The sequential operation is preferably controlled by a microprocessor or other central processing unit to electronically instruct the valve processor 40 to sequentially actuate the valves 38a–38d. Electronic control using the valve processor 40 allows precise valve actuation control for sequencing and valve actuation duration.

For example, using a 7 French size catheter 14, it has been found that 1300 cubic centimeters per minute of coolant can create a 28 millimeter long freeze area. By sequentially applying the 1300 cubic centimeter per minute coolant to each of the four injection lumens 30a–30d in a manner which causes an overlap of the freeze area, a freeze area of approximately 100 millimeters in length can be created.

As such, a freeze length L can be achieved using a very small cryogenic fluid flow rate as compared with known devices (3800 cubic feet per minute to achieve a 60 millimeter freeze length using a single injection lumen versus 1300 cubic centimeter per minutes cryogenic fluid flow rate to achieve a 100 millimeter freeze length L). The arrangement of the present invention advantageously conserves cryogenic fluid while providing an extended freeze length L as compared with known similarly sized devices.

As eluded to above, in order to preserve the advantage of cryoablation by adhering the thermally transmissive tip region 16 to the patient's tissue during the ablation procedure, the ejection of cryogenic fluid from one injection lumen should begin after cryogenic fluid ejection is terminated in the previous injection lumen in the sequence, but before the previous areas dislodge, i.e. thaw, from the tissue. Because the sequential application of cryogenic fluid is used, the total procedure time becomes t times m where m is the number of freezing areas (and injection tubes).

It is also contemplated that multiple lumens can be logically grouped and activated at substantially the same time, subject to maintaining a cryogenic fluid flow rate which can be evacuated from the catheter 14 while maintaining a negative pressure within the catheter 14. For example, valves 38a and 38c can be opened at substantially the same time, then closed and valves 38b and 38d opened at substantially the same time. This technique shortens the cryoablation procedure time as compared with the discreet sequential operation of the valves 38a–38d described above while still maintaining a safe operating environment, for example, 2600 cubic centimeters per minute in a 7 French size catheter.

Another implementation of the device of the present invention permits use as a mapping and/or selective ablation zone device. Because the freeze area length along the tip of the device is extremely elongated as compared with known devices and because particular areas of the device can be selectively cooled (areas 64a–64d), the device of the present invention can be used to perform cold mapping to detect tissue regions, such as cardiac tissue regions, which if ablated will eliminate an arrhythmia. Each of areas 64a–64d can be cooled to determine which areas, if any, will improve or eliminate the arrhythmia.

The elongated freeze length L advantageously allows individual areas to be cooled without the need to relocate the thermally transmissive tip region 16 to another tissue point. Once an area is identified as suitable for ablation, the particular valve or valves 38 are opened and the specific section(s) of the thermally transmissive tip region 16 cooled. This arrangement advantageously minimizes tissue destruction such as myocardial tissue destruction and saves time by avoiding the need to repeatedly thaw and relocate the thermally transmissive tip region 16.

Although the present invention is described above with respect to a catheter, it is contemplated that a device constructed in accordance with the principles of the present invention can take other forms, including but not limited to a rigid probe.

The present invention advantageously provides a device and method which provides an elongated freeze length within the thermally transmissive tip region in a manner in which specific areas in the thermally transmissive tip region can be cooled or sequentially cooled to provide an elongated freeze length. The arrangement of the present invention is advantageously provided in a manner which maintains a usable device size and which maintains a safe operating mode by maintaining a negative pressure within the device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A device for cryosurgical ablation, comprising:
   a tip having a thermally transmissive region along a length thereof, the thermally transmissive region being operable at a temperature sufficient to cryosurgically ablate tissue in contact therewith;
   a plurality of cryosurgical fluid injection lumens, each of the plurality of cryosurgical injection lumens having a first end positioned within the tip at a different point along the length of the thermally transmissive region,
   each of the first ends being arranged to cool overlapping respective portions along the length of the thermally transmissive region when cryogenic fluid is ejected from the plurality of cryogenic fluid injection lumens,
   wherein each of the plurality of cryogenic fluid injection lumens further comprises a second end opposite the first end, and wherein the device further comprises a plurality of valves, each of the plurality of valves having an output in fluid communication with the second end of a corresponding cryogenic fluid injection lumen.

2. The device according to claim 1, wherein the plurality of valves are electrically actuable.

3. The device according to claim 1, wherein the device further comprises a handle having an inner volume and wherein each of the plurality of valves processor is positioned within the inner volume.

4. The device according to claim 1, further comprising a cryogenic fluid distributor, the cryogenic fluid distributor having:
   an input for receiving a flow of cryogenic fluid; and
   a plurality of outputs in fluid communication with a respective valve,
   the cryogenic fluid distributor receiving the flow of cryogenic fluid and substantially evenly distributing the flow of cryogenic fluid to each of the plurality of valves.

5. The device according to claim 4, wherein the device further comprises a handle having an inner volume and wherein the fluid distributor is positioned within the inner volume.

6. The device according to claim 1, wherein the plurality of valves are individually sequentially actuable.

7. A device for cryosurgical ablation, comprising:
   a tip having a thermally transmissive region along a length thereof, the thermally transmissive region being operable at a temperature sufficient to cryosurgically ablate tissue in contact therewith;
   a plurality of cryosurgical fluid injection lumens, each of the plurality of cryosurgical injection lumens having a first end positioned within the tip at a different point along the length of the thermally transmissive region,
   each of the first ends being arranged to cool overlapping respective portions along the length of the thermally transmissive region when cryogenic fluid is ejected from the plurality of cryogenic fluid injection lumens,
   wherein each of the plurality of cryogenic fluid injection lumens further comprises a second end opposite the first end, and wherein the device further comprises a valve assembly having:
   a plurality of electrically actuable valves, each of the plurality of electrically actuable valves having an output in fluid communication with the second end of a corresponding cryogenic fluid injection lumen; and
   a valve processor, the valve processor receiving at least one electronic valve actuation signal and controlling the actuation of the plurality of valves in accordance with the received at least one electronic valve actuation signal.

8. The device according to claim 7, wherein the plurality of electrically actuable valves are piezo-electric valves.

9. The device according to claim 7, wherein the device further comprises a handle having an inner volume and wherein the valve processor is positioned within the inner volume.

10. The device according to claim 7, further comprising a cryogenic fluid distributor, the cryogenic fluid distributor having:
   an input for receiving a flow of cryogenic fluid; and
   plurality of outputs in fluid communication with a respective valve within the valve assembly,
   the fluid distributor receiving the flow of cryogenic fluid and substantially evenly distributing the flow of cryogenic fluid to each of the plurality of valves within the valve assembly.

11. The device according to claim 10, wherein the device further comprises a handle having an inner volume and wherein the fluid distributor is positioned within the inner volume.

12. The device according to claim 7, wherein the valve processor is operable to sequentially actuate the plurality of valves.

13. A device for cryosurgical ablation, comprising:
   a tip having a thermally transmissive region along a length thereof, the thermally transmissive region being operable at a temperature sufficient to cryosurgically ablate tissue in contact therewith;
   a plurality of cryosurgical fluid injection lumens, each of the plurality of cryosurgical injection lumens having a first end positioned within the tip at a different point along the length of the thermally transmissive region,
   each of the first ends being arranged to cool overlapping respective portions along the length of the thermally transmissive region when cryogenic fluid is ejected from the plurality of cryogenic fluid injection lumens,
   wherein each of the plurality of cryogenic fluid injection lumens further comprises a second end opposite the first end, and wherein the device further comprises an integrated fluid provisioning unit having:
      a valve assembly, the valve assembly including:
         a plurality of electrically actuable valves, each of the plurality of electrically actuable valves having an output in fluid communication with the second end of a corresponding cryogenic fluid injection lumen; and
         a valve processor, the valve processor receiving at least one electronic valve actuation signal and controlling the actuation of the plurality of electrically actuable valves in accordance with the received at least one electronic valve actuation signal; and
      a cryogenic fluid distributor, the cryogenic fluid distributor having:
         an input for receiving a flow of cryogenic fluid; and
         a plurality of outputs in fluid communication with a respective electrically actuable valve,
         the fluid distributor receiving the flow of cryogenic fluid and substantially evenly distributing the flow of cryogenic fluid to each of the plurality of electrically actuable valves.

14. The device according to claim 13, wherein the valve processor operates to sequentially actuate the plurality of valves.

15. The device according to claim 13, wherein the device further comprises a handle having an inner volume and wherein the integrated fluid provisioning unit is positioned within the inner volume.

16. A method for cryosurgically ablating tissue, the method comprising:
   positioning a cryosurgical tip at tissue to be ablated, the tip having a thermally transmissive region along a length thereof; and
   sequentially injecting cryogenic fluid into the tip through a plurality of cryogenic fluid injection lumens terminating within the tip at different points along the length of the thermally transmissive region,
   wherein the cryogenic fluid is sequentially injected into the tip by sequentially actuating a plurality of valves in fluid communication with a corresponding cryogenic fluid injection lumen.

17. The method according to claim 16, wherein the plurality of valves are sequentially actuated in accordance with an electronic signal.

18. The method according to claim 17, wherein the plurality of valves are piezo-electrically operated.

19. A method for cryosurgically ablating tissue, the method comprising:
   positioning a cryosurgical tip at tissue to be ablated, the tip having a thermally transmissive region along a length thereof; and
   sequentially injecting cryogenic fluid into the tip through a plurality of cryogenic fluid injection lumens terminating within the tip at different points along the length of the thermally transmissive region,
   wherein the plurality of injection lumens are arranged into a plurality of groups, and wherein the cryogenic fluid is sequentially injected into the plurality of groups of injection lumen,
   wherein the cryogenic fluid is sequentially injected into the tip by sequentially actuating groups of valves in fluid communication with the corresponding groups of cryogenic fluid injection lumen.

20. A method for using cryogenic mapping to detect an arrhythmia in cardiac tissue, the method comprising:
   positioning a cryosurgical tip at tissue to be mapped, the tip having a thermally transmissive region along a length thereof; and
   sequentially injecting cryogenic fluid into the tip through a plurality of cryogenic fluid injection lumens terminating within the tip at different points along the length of the thermally transmissive region to cryogenically map the tissue.

* * * * *